(12) United States Patent
Wright et al.

(10) Patent No.: US 9,791,390 B2
(45) Date of Patent: Oct. 17, 2017

(54) DEVICES AND SYSTEMS FOR SPATIAL AVERAGING OF ELECTRON BACKSCATTER DIFFRACTION PATTERNS

(71) Applicant: EDAX, Incorporated, Mahwah, NJ (US)

(72) Inventors: Stuart Ian Wright, St. George, UT (US); Matthew McBride Nowell, Riverton, UT (US); Scott Perry Lindeman, Lehi, UT (US); Patrick Paul Camus, Pen Argyl, PA (US)

(73) Assignee: EDAX, Incorporated, Mahwah, NJ (US)

( * ) Notice: Subject to any disclaimer, the term of this patent is extended or adjusted under 35 U.S.C. 154(b) by 86 days.

(21) Appl. No.: 15/004,511

(22) Filed: Jan. 22, 2016

(65) Prior Publication Data

US 2016/0216219 A1     Jul. 28, 2016

Related U.S. Application Data

(60) Provisional application No. 62/106,628, filed on Jan. 22, 2015, provisional application No. 62/196,089, filed on Jul. 23, 2015.

(51) Int. Cl.
*G06K 9/00* (2006.01)
*G01N 23/20* (2006.01)

(52) U.S. Cl.
CPC .............. *G01N 23/20058* (2013.01)

(58) Field of Classification Search
CPC .. G01N 23/20058; A01N 47/36; A01N 25/12; A01N 41/10; H01L 29/7869; H01L 29/66969
USPC ................ 382/108; 148/412, 685; 439/887; 428/546, 323; 216/95; 420/591; 427/250
See application file for complete search history.

(56) References Cited

U.S. PATENT DOCUMENTS

| | | | |
|---|---|---|---|
| 8,951,369 B2* | 2/2015 | Maki | C22C 9/04 148/412 |
| 2015/0284852 A1* | 10/2015 | Pokroy | C23F 1/40 428/546 |

* cited by examiner

*Primary Examiner* — Charlotte M Baker
(74) *Attorney, Agent, or Firm* — Ray Quinney & Nebeker, P.C.; John O. Carpenter

(57) ABSTRACT

A diffraction pattern is averaged with adjacent diffraction patterns to increase a signal to noise ratio thereof and improve indexing accuracy. The pixels of a diffraction pattern image are averaged with a correlated pixel from one or more adjacent diffraction patterns. Noise artifacts are reduced in intensity, while signals present in each of the patterns reinforce one another to produce an averaged diffraction pattern which is then indexed.

20 Claims, 14 Drawing Sheets

DEVICES AND SYSTEMS FOR SPATIAL AVERAGING OF ELECTRON BACKSCATTER DIFFRACTION PATTERNS

CROSS-REFERENCE TO RELATED APPLICATIONS

The present disclosure claims priority to and the benefit of U.S. Provisional Application No. 62/106,628 filed Jan. 22, 2015 and entitled "DEVICES AND SYSTEMS FOR SPATIAL AVERAGING OF ELECTRON BACKSCATTER DIFFRACTION PATTERNS," the disclosure of which is incorporated herein by reference in its entirety, and to U.S. Provisional Application No. 62/196,089 filed Jul. 23, 2015 and entitled "DEVICES AND SYSTEMS FOR SPATIAL AGGREGATION OF SPECTRAL ANALYSIS FROM ELECTRON MICROSCOPES", the disclosure of which is incorporated herein by reference in its entirety.

BACKGROUND OF THE DISCLOSURE

Electron Backscatter Diffraction ("EBSD") and x-ray spectrometry have grown into robust analytic techniques for the measurement of material properties. EBSD, energy dispersive spectrometry ("EDS"), and wavelength dispersive spectrometry ("WDS") are analytical techniques performed in a scanning electron microscope ("SEM") in a low pressure or near vacuum environment. A sample is positioned beneath a column housing an electron source. The electron source may be any suitable source, such as a tungsten filament, thermal field emission, or $LaB_6$ electron source. The electron source may emit electrons that are directed in a beam through the column and toward a sample chamber. The sample chamber may be connected to the column and allow a sample to be held in line with the electron beam for imaging.

EBSD conventionally images crystallographic orientations from a prepared surface that is substantially flat and free of deformation from the preparation (i.e., polishing). EDS conventionally images surfaces in which an interaction volume of the electron beam interacts with the desired sample region. The sample may have an unprepared surface allowing sampling of the exposed surface (e.g., particles or broken and/or cut surfaces) or a prepared surface that is substantially flat. Non-conductive samples may be made more conductive by deposition of a conductive layer over at least part of the surface in order to provide a conductive path to ground. For example, carbon layers or gold layers sputtered onto the surface of a sample can provide a conductive layer that dissipates charge from the sample to the sample stage or other ground within the sample chamber.

BRIEF SUMMARY OF THE DISCLOSURE

This summary is provided to introduce a selection of concepts that are further described below in the detailed description. This summary is not intended to identify specific features of the claimed subject matter, nor is it intended to be used as an aid in limiting the scope of the claimed subject matter.

In a first embodiment, a method for spatially averaging diffraction patterns includes acquiring a central diffraction pattern and a plurality of adjacent diffraction patterns from an electron backscatter diffraction detector. Acquiring the central diffraction pattern and the plurality of adjacent diffraction patterns may be during live acquisition or from a saved diffraction pattern set. The method includes averaging the central diffraction pattern with one or more of the plurality of adjacent diffraction patterns to produce an averaged diffraction pattern and indexing the averaged diffraction pattern to produce an averaged crystal orientation.

In a second embodiment, a system for spatially averaging diffraction patterns includes an electron backscatter detector, one or more hardware processors, and one or more storage devices. The one or more storage devices have instructions stored thereon that, when performed by the one or more hardware processors, perform a method including acquiring and indexing a central diffraction pattern to produce a measured crystallographic orientation. The method then includes acquiring a plurality of adjacent diffraction patterns and indexing at least one of the adjacent diffraction patterns to produce an adjacent crystallographic orientation. Comparing the measured crystallographic orientation with the adjacent crystallographic orientation allows only adjacent diffraction patterns within a misorientation tolerance to be averaged with the central diffraction pattern to produce an averaged diffraction pattern. The averaged diffraction pattern is then indexed.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which.

DETAILED DESCRIPTION

Figure 1:
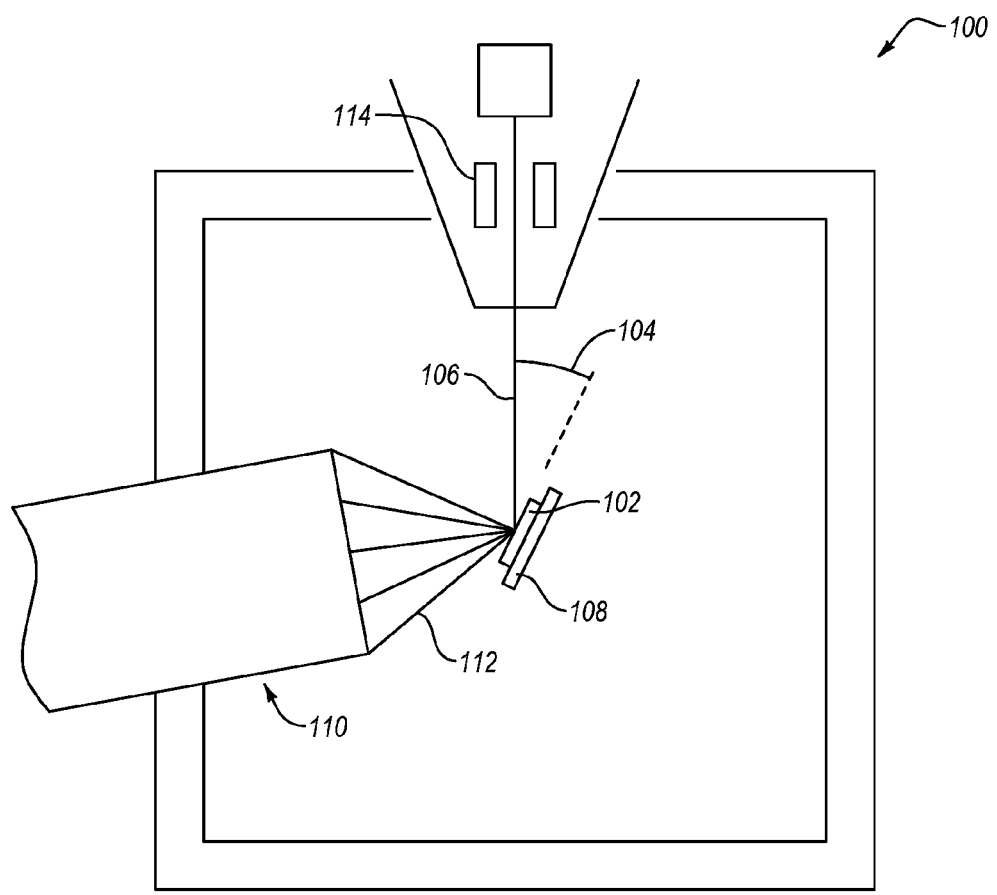
FIG. 1 depicts an embodiment of conventional electron backscatter diffraction ("EBSD") pattern collection in a scanning electron microscope ("SEM"), according to at least one embodiment described herein.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

An electron backscatter detector ("EBSD") detector may collect a diffraction pattern using an image generation surface and an image collection device. For example, an image collection device, such as a charge-coupled device ("CCD"), may be positioned near an end of the EBSD detector proximate a crystalline sample in a scanning electron microscope ("SEM"). The image collection device may be situated behind (i.e., farther from the sample) an image generation surface. The image generation surface may generate a signal and/or image visible to the image collection device based on the presence of electrons at or near the image generation surface. For example, a scintillator may receive incident electrons and re-emit light. The light may be collectable by the image collection device. In another example, direct electron detection may be used to generate and/or collect a diffraction pattern image without the generation of light. Electrons from an electron beam may be diffracted toward the image generation surface by a plurality of crystal planes in the sample. The repeating crystal planes of the sample may diffract the electrons in an array of geometrically related "bands" of electrons. The electron bands may strike the image generation surface, and may be collected by the image collection device.

The electron beam may interact with the crystal lattice of the sample at the surface and in a subsurface interaction volume. A crystal orientation of the crystal lattice may be calculated from the resulting diffracted electrons. A diffraction pattern comprising a plurality of electron bands may be measured and an orientation calculated based on known lattice parameters for the sampled crystal lattice and the relative location of detected electron bands in the pattern. In some samples, the quality of the diffraction may be less than desired. For example, the signal-to-noise ratio of the electron bands, the contrast in the image, or other image quality degradation may compromise accurate detection of electron bands within the diffraction pattern.

In some instances, a degradation in image quality may be localized or may be at least partially related to dwell time. A central diffraction pattern may be averaged with one or more adjacent diffraction patterns collected at adjacent data points to the central diffraction pattern. In some embodiments, the averaging of a central diffraction pattern with adjacent diffraction patterns from adjacent data points may reduce noise in the diffraction pattern image and reinforce the signal shown in the diffraction pattern. In other embodiments, a crystal orientation may be calculated as best as possible for each of the adjacent diffraction patterns prior to averaging to limit or prevent the averaging of diffraction patterns from different crystal lattices (e.g., a different grain of the sample).

An energy dispersive spectrometry ("EDS") detector may detect x-rays and measure the energy and quantity of the detected x-rays. For example, an EDS detector may have a detection surface, such as a semiconductor, that may react when an x-ray emitted by a sample contacts the detection surface. The detection surface may generate a voltage signal when an x-ray strikes the detection surface. The voltage signal may be measured to calculate the energy of the incident x-ray. The energy of the incident x-ray correlates to the atom of the sample that emitted the x-ray.

Additionally, while the methods described herein are described in relation to an EDS detector, at least some of the methods may be conducted using wavelength dispersive spectrometry ("WDS"). WDS detectors may detect emitted x-rays similarly to an EDS detector, but use one or more diffraction crystals to measure the wavelength of the emitted x-ray to calculate the energy of the x-ray.

As shown in FIG. 1, conventional EBSD may be conducted in an SEM 100 by presenting a sample 102 at an angle 104 to an electron beam 106. The angle 104 may be any angle within a range of values from 5° to 50° degrees and most commonly, 20° to the beam. The position of the sample 102 relative to the beam 106 may be achieved by tilted a sample stage 108 approximately 70° from level or by providing a sample holder (not shown) having non-parallel surfaces mounted to the sample stage 108 or a combination of the two. The angle 104 of the sample 102 relative to the beam 106 allows electrons from the beam 106 to enter a portion of the sample 102. In the portion of the sample, known as the interaction volume, electrons diffract from crystal planes inside the sample 102. The electrons travel from the interaction volume toward a detector 110 in a geometric pattern of relative intensities of diffracted electrons 112. The diffracted electrons 112 may be measured to calculate the relationship of crystal planes within the interaction volume and, therefore, an orientation of the crystal planes in space relative to the sample surface or other known orientation.

Lenses 114, such as electromagnetic lenses, may focus and/or deflect the electron beam 106 at different working distances (focal length beneath a lowest point of the column) and/or locations on the sample 102. A "scan" of the SEM 100 may include construction of an image of a surface of the sample 102 by rastering the beam 106 through a predetermined range of positions and/or deflections of the beam 106. A combination of the EBSD detector 110 and rastering of the beam 106 allow for the construction of orientation maps of a portion of the sample 102. An orientation map may allow for the measurement of grain size, grain aspect, plastic deformation, orientation distribution, texture measurements, phase relationships, transformations, grain boundary relationships, and other properties. Additionally, the orientation map may allow visualization of the spatial relationship of the measurements. While at least partially dependent on the SEM and settings (e.g., accelerating voltage, beam current, pressure in the chamber, etc.) used, EBSD in an SEM may allow for grain resolution down to 100 nm or less on bulk samples.

Collection rates for individual diffraction patterns may range from 2 seconds per pattern to well over a 1000 patterns per second. The collection rate of the EBSD detector 110 may depend at least partially upon the settings of the SEM 100 and the settings and/or specifications of the EBSD detector 110. The collection rate of the EBSD detector 110 may also depend at least partially upon the sample from which orientations are measured. The diffraction volume may produce less than ideal diffraction patterns due to a number of factors, including poor surface preparation, fine grain size, deformation, hydrocarbon contamination, oxide surface layers, or combinations thereof. For example, a longer dwell time may be necessary to achieve satisfactory contrast in the collected diffraction pattern or a sufficient signal to noise ratio to measure and calculate an orientation of the sample 102 where the beam 106 meets the sample 102. In many laboratories, instrument time is a priority, therefore increasing collection speed and increasing high confidence orientation measurement rates on a variety of sample types may be desirable.

Figure 2:
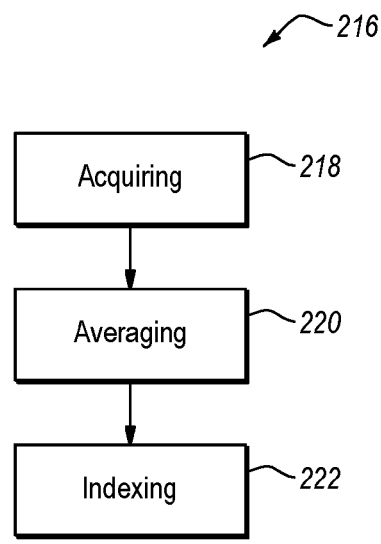
FIG. 2 depicts a method of spatially averaging diffraction patterns, according to at least one embodiment described herein.

FIG. 2 depicts a flowchart of a method 216 for spatially averaging diffraction patterns. The method 216 may include acquiring 218 a plurality of diffraction patterns from a sample, including a central diffraction pattern and adjacent diffraction patterns from locations ("adjacent locations") adjacent a location ("central location") of the central diffraction pattern. In some embodiments, acquiring 218 a plurality of diffraction patterns may include live acquisition. As used herein, "live acquisition" should be understood to include focusing an electron beam on a location on a sample surface, detecting the diffracted electrons escaping a crystal lattice of the sample using an image generation surface, and imaging the detected electrons using an image collection device. In other embodiments, acquiring 218 a plurality of diffraction patterns may include rescanning a saved pattern set, the saved pattern set having been collected during live acquisition with each location of the saved pattern set including at least an image of the diffraction pattern from the location and a coordinate of the location. As used herein, "rescanning" should be understood to include loading a saved pattern set including a plurality of images of diffraction patterns from a data storage device, ordering the plurality of images based upon collection coordinates assigned during live acquisition, and loading a selected image of a diffraction pattern from the dataset.

The method 216 may include averaging 220 the central diffraction pattern with one or more of the adjacent diffraction patterns. In some embodiments, averaging of the central diffraction pattern may include averaging the diffraction images. For example, a central diffraction pattern may be averaged with one or more adjacent diffraction patterns by averaging the brightness of each pixel in the diffraction pattern images. A diffraction pattern image may include a plurality of pixels. A pixel may have a brightness and/or intensity value. A pixel in the central diffraction pattern may have a first brightness. A pixel located at an associated positioned in an adjacent diffraction pattern may have a second brightness. The first brightness and second brightness may be averaged to produce an averaged pixel with an averaged brightness. Each of the pixels in a central diffraction pattern and one or more adjacent diffraction patterns may be averaged in such a way to produce an averaged diffraction pattern with a plurality of pixels having averaged brightnesses.

In another embodiment, a central diffraction pattern may be averaged with one or more adjacent diffraction patterns by averaging the measured positions of electron bands. Each diffraction pattern (as will be described in relation to FIG. 3) may have one or more electron bands. A best fit line may be assigned to an electron band by evaluating the intensity of neighboring pixels in a diffraction pattern image and approximating the orientation of an electron band based at least partially upon a path of highest intensity. The measured positions of electron bands in a central diffraction pattern may be averaged with one or more adjacent diffraction patterns by assigning a polar coordinate value to the position of each identified electron band in a diffraction pattern.

The method 216 may also include indexing 222 the averaged diffraction pattern produced by averaging the central diffraction pattern with one or more adjacent diffraction patterns. As used herein, "indexing" should be understood to refer to the calculation of one or more crystal orientations at which the sampled portion of the crystal lattice may be oriented relative to a surface of the sample. In some embodiments, the orientation of the crystal lattice may be calculated relative to another reference frame. For example, a user may desire the orientation to be calculated relative to a transverse axis of the sample surface, such as when evaluating texture or preferred crystallographic orientations in extruded materials in longitudinal cross-section.

Indexing 222 a diffraction pattern may include detecting at least three electron bands in a diffraction pattern, such as the averaged diffraction pattern, selecting a plurality of sets of three electron bands ("a triplet") from the at least three electron bands, and calculating a one or more crystallographic orientations for each triplet based on known lattice parameters. For example, a diffraction pattern having five detected electron bands may have ten triplets. A single triplet may provide a plurality of crystallographic orientations. Indexing 222 a diffraction pattern may include determining the orientation calculated most frequently based on the plurality of triplets.

A confidence index may be calculated during indexing 222. The confidence index may be a weighted ratio of the most likely orientation and a second-most likely orientation. A crystal lattice may exhibit various forms of symmetry. The symmetry of the crystal lattice may manifest as symmetry in the diffraction pattern. Symmetry in the diffraction pattern may lead a single triplet to provide multiple possible orientations of a crystal lattice that may correspond to the measured triplet. Therefore, a single triplet alone may lead to ambiguity and/or "false positives." However, taken in aggregated, multiple triplets may align with a one orientation more often than a second orientation. A confidence index may reflect the rate at which a "correct" orientation is calculated to match the detected triplets versus a "false positive." A confidence index may be calculated by $$CI = (V_1 - V_2)/V_{Ideal} \quad (1)$$

where CI is the confidence index; $V_1$ and $V_2$ are the number of triplets that may correspond to the most likely orientation and the second-most likely orientation, respectively; and $V_{Ideal}$ is the total possible number of triplets that may correspond to an orientation (i.e., the total number of detected triplets). The confidence index may allow a user to determine the level of ambiguity in a system exhibiting symmetry.

Figure 3:
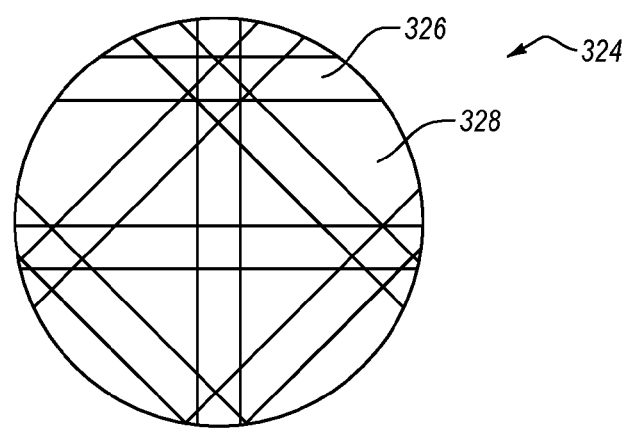
FIG. 3 depicts a diffraction pattern, according to at least one embodiment described herein.

FIG. 3 depicts an embodiment of a diffraction pattern 324 according to the present description. The depicted diffraction pattern 324 is merely representative of a possible diffraction pattern and should not be understood to limit the present disclosure regarding crystal group or orientation. The diffraction pattern 324 may exhibit areas of high electron concentration and areas of lower electron concentration. The high electron concentration may manifest as a brighter electron band 326 and the lower electron concentration may manifest as darker region 328 between the electron bands 326. As described herein, "brighter" and "darker" should be understood to refer to the relative appearance of the electron concentrations after interaction with an image generation surface, such as a phosphor scintillator.

The electron bands 326 may exhibit a higher concentration of electrons due to the diffraction of electrons from the repeating crystal planes of a crystal lattice. The repeating crystal planes may diffract incident electrons from an electron beam toward an EBSD detector. The diffraction may create regions of higher and lower electron intensity due, at least partially, to constructive and deconstructive interference of the electrons having different paths lengths relative to the lattice parameters. The darker regions 328 may exhibit some electron interactions due to electrons scattered toward the EBSD detector without exhibiting diffraction.

The diffraction pattern 324 may exhibit variations in intensity across the pattern for reasons unrelated to diffraction of the electrons from the crystal lattice. For example, diffraction patterns may exhibit intensity variations due to deformation of the crystal lattice. In an ideal example, the crystal lattice may be undeformed and may have repeating crystal planes which are parallel and evenly spaced, providing ideal diffraction surfaces from which the incident electrons may diffract. In a deformed sample, one or more bonds in the crystal lattice may be strained such that one or more crystal planes are misaligned. As used herein, "misaligned" should be understood refer to a crystal plane in a plurality of crystal planes that is not parallel to the other crystal planes. The one or more misaligned planes may limit the constructive and deconstructive interference of the diffracted electrons, and may decrease contrast in a diffraction pattern. Decreased contrast in a diffraction pattern may reduce the signal to noise ratio of the pattern and limit the number of detectable electron bands 326 and/or the accurate detection of the electron bands 326.

Figure 4:
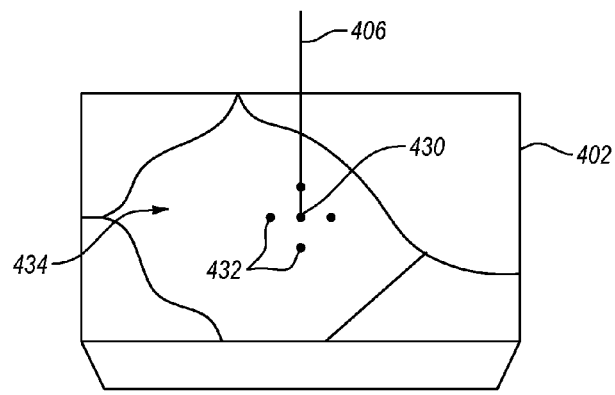
FIG. 4 depicts a plurality of sampling locations on a sample surface, according to at least one embodiment described herein.

FIG. 4 illustrates a sample 402 and an incident electron beam 406 focused on a central sampling location 430, according to at least one embodiment described herein. The central sampling location 430 may be approximated as a point on a surface of the sample 402, but may vary in size depending on the settings and configuration of the electron beam 406. For example, the source of the electron beam 406 may be a thermal field emission source, a tungsten-filament source, or another electron source. A thermal field emission source may produce an electron beam having a diameter less than 5 nanometers when properly calibrated, focused, and stigmated. A tungsten-filament source may produce an electron beam having a diameter greater than about 30 nanometers when properly calibrated, focused, and stigmated. The central sampling location 430 may also include interactions between the electron beam 406 and the sample 402 that occur below the surface of the sample 402. For example, the central sampling location 430 may include an interaction volume. The interaction volume may be determined, at least partially by the accelerating voltage and current of the electron beam 406 and the sample 402 (e.g., material type and/or sample preparation).

A central sampling location 430 may be proximate one or more adjacent sampling locations 432, shown in FIG. 4 as being positioned according to a rectangular grid. In other embodiments, the one or more adjacent sampling locations 432 may be defined according to a hexagonal grid, a pentagonal grid, octagonal grid, or other repeating system. A distance between a center point of the central sampling location 430 and the one or more adjacent sampling locations 432 may be understood to be a "step size" between the sampling locations. In some embodiments, the one or more adjacent sampling locations 432 may be immediately adjacent the central sampling location 430 based upon a step size that is approximately equal a nominal diameter of the electron beam 406. In other embodiments, the one or more adjacent sampling locations 432 may be immediately adjacent the central sampling location 430 based upon a step size that is approximately equal a simulated interaction volume of the electron beam 406 within the sample 402 (e.g., a Monte Carlo simulation). In yet other embodiments, the one or more adjacent sampling locations 432 may be adjacent the central sampling location 430 based upon a step size for an automated sampling grid that is selected by a user based on one or more dimensions of the sample 402, a desired diffraction pattern set size, collection duration, other factors, or combinations thereof.

FIG. 4 shows a central sampling location 430 and a plurality of adjacent sampling locations 432 within a grain 434 of the sample 402. As used herein, a grain 434 should be understood to include any crystalline structure with a continuous crystal lattice. For example, a grain 434 may be deformed and may exhibit strain within the crystal lattice leading to misaligned planes and/or dislocations within the crystal lattice while still having a continuous crystal lattice.

Figure 5:
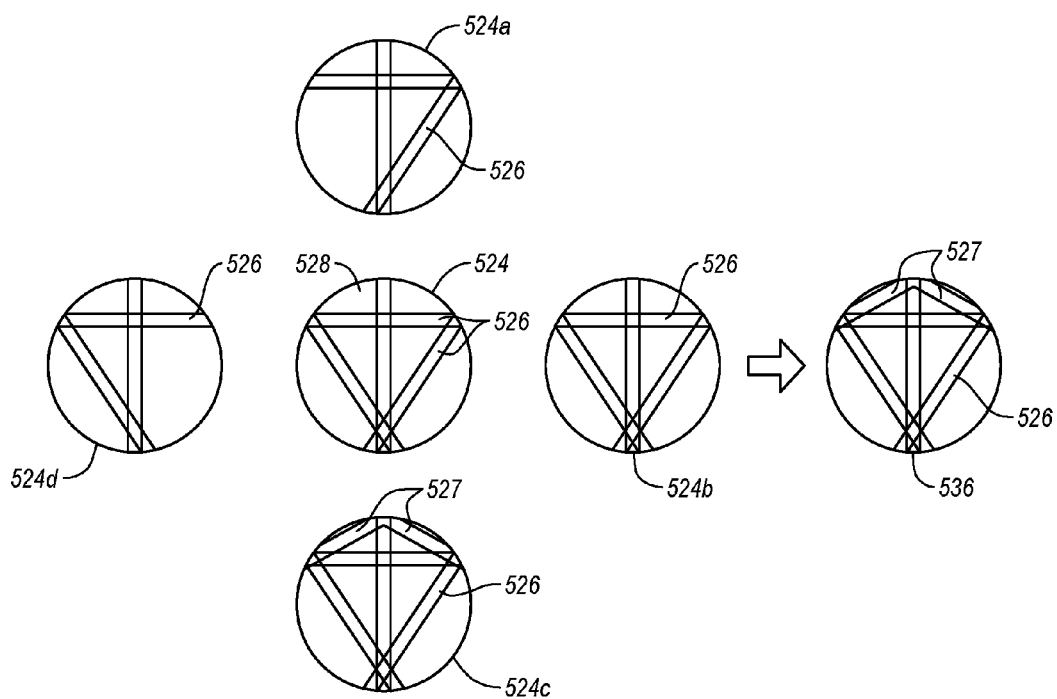
FIG. 5 is a schematic representation of spatially averaging diffraction patterns, according to at least one embodiment described herein.

FIG. 5 schematically depicts the averaging of central diffraction pattern 524 with a plurality of adjacent diffraction patterns 524a-d. The central diffraction pattern 524 may be acquired from a central sampling location, and the plurality of adjacent diffraction patterns 524a-d may be acquired from a plurality of adjacent sampling locations, such as described in relation to FIG. 4. FIG. 5 depicts a central diffraction pattern 524 having four electron bands 526. The first adjacent diffraction pattern 524a has three electron bands 526, which correlate with three of the four electron bands 526 in the central diffraction pattern 524. The second adjacent diffraction pattern 524b has four electron bands 526, which correlate with the electron bands 526 in the central diffraction pattern 524. The third adjacent diffraction pattern 524c has six electron bands 526, which correlate with the electron bands 526 in the central diffraction pattern 524 and include two additional electron bands 527 unobserved in the central diffraction pattern 524. The fourth adjacent diffraction pattern 524a has three electron bands 526, which correlated with three of the four electron bands 526 in the central diffraction pattern 524. The electron bands 526 may be areas of high brightness on the diffraction patterns.

The central diffraction pattern 524 and the plurality of diffraction patterns 524a-d may comprise a plurality of pixels. As described herein, the pixels may have a brightness value and a pixel location value within a diffraction pattern image, which may have a pattern location value for the sampling location at which the pattern was acquired. Any pixel of the central diffraction pattern 524 and a pixel of the plurality of diffraction patterns 524a-d having the same pixel location value may be averaged according to:

$$I_{x,y} = (1/N)^*(I_{x,y} + I_{x-1,y} + I_{x+1,y} + I_{x,y-1} + I_{x,y+1}) \quad (2)$$

where I is the intensity or brightness of a pixel. x and y are the x- and y-direction coordinates of the pattern location value. N is the quantity of diffraction patterns being averaged. The process may be repeated for all pixels having the same pixel location value in the diffraction patterns. The averaging of all of the pixels in the central diffraction pattern 524 with the pixels having the same pixel location values in the one or more adjacent diffraction patterns 524a-d may produce an averaged diffraction pattern 536. The averaged diffraction pattern 536 may exhibit the electron bands 526 of the central diffraction pattern 524 and may include the two additional electron bands 527 of the third adjacent diffraction pattern 524c that are unobserved in the central diffraction pattern 524. The two additional electron bands 527 in the averaged diffraction pattern 536 may be less bright than the electron bands 526 of the central diffraction pattern 524 due, at least partially to the averaging of the two additional electron bands 527 with the darker region 528. The additional electron bands 527 in the averaged diffraction pattern 536 may contribute to the indexing of the averaged diffraction pattern 536, and may reduce ambiguity or allow indexing where an orientation was not able to be calculated previously.

In some embodiments, the central diffraction pattern 524 and/or the one or more adjacent diffraction patterns 524a-d may have noise and/or false positives. Noise and/or false positives in the central diffraction pattern 524 and/or the one or more adjacent diffraction patterns 524a-d may be reduced in brightness and/or intensity by the averaging process described herein. For example, in a diffraction pattern having low signal to noise ratio, a pixel location value having a high brightness value in one the diffraction patterns may be averaged to a lower brightness value. The reduction of noise may allow electron bands to be properly identified, including electron bands having lower overall brightness compared to other electron bands such as the additional electron bands 527 in the averaged diffraction pattern 536.

Figure 6:
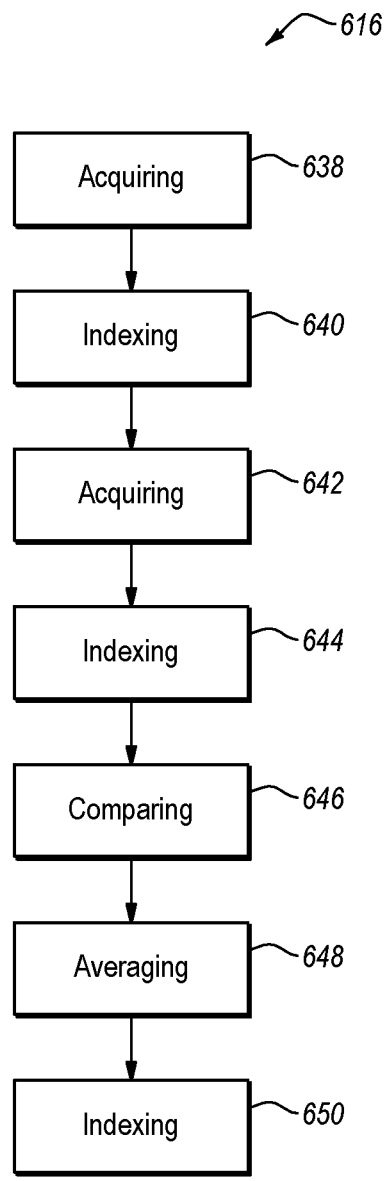
FIG. 6 depicts a method of spatially averaging correlated diffraction patterns, according to at least one embodiment described herein.

FIG. 6 depicts another embodiment of a method 616 for spatially averaging diffraction patterns. The method 616 may include acquiring 638 a central diffraction pattern and indexing 640 the central diffraction pattern. The method 616 may continue by acquiring 642 one or more adjacent diffraction patterns and indexing 644 the one or more adjacent diffraction patterns. Comparing 646 the calculated crystallographic orientation of the central diffraction pattern and calculated crystallographic orientations of the one or more adjacent diffraction patterns may allow the averaging 648 of the central diffraction pattern with the adjacent diffraction patterns that provide a calculated crystallographic orientation within a user-defined misorientation tolerance of the calculated crystallographic orientation of the central diffraction pattern. For example, the user-defined misorientation tolerance may be 3°. In other examples, the user-defined misorientation tolerance may be 5°. In yet other examples, the user-defined misorientation tolerance may be 10°. After averaging 648 to produce an averaged diffraction pattern, the method 616 may further include indexing 650 the averaged diffraction pattern. In some embodiments, the method 616 may include comparing a confidence index of the calculated crystallographic orientation of the averaged diffraction pattern against a confidence index of the calculated crystallographic orientation of the central diffraction pattern as a verification routine to check for introduction of ambiguity during the averaging process.

In some embodiments, indexing 640 of the central diffraction pattern and/or indexing 644 of one or more of the adjacent diffraction patterns may not be possible due to shadowing, poor signal to noise ratio, low contrast, unknown or unexpected lattice parameters (e.g., an unexpected, low symmetry phase such as a precipitate), or combinations thereof. Comparing 646 the calculated crystallographic orientation of the central diffraction pattern and calculated crystallographic orientations of the one or more adjacent diffraction patterns may not be possible or reliable. In such embodiments, the method 616 may include comparing 646 a pixel intensity of the central diffraction pattern to a pixel intensity of one or more adjacent diffraction patterns.

As described herein, an acquired diffraction pattern image may have a plurality of pixels therein. Each pixel may have an intensity and/or brightness value and a pixel location value. The pixel location value may be unique to a pixel within a diffraction pattern image and allow the correlation of a first pixel in a first diffraction pattern image to a second pixel in a second diffraction pattern image. For example, a first pixel and a second pixel may have the same pixel location value (e.g., 0,1). The first pixel and second pixel may have the substantially same or different brightness values. For example, the first pixel may be considered to be substantially the same as a second pixel when a first brightness value of the first pixel is falls within a brightness tolerance value (i.e., is between 0% and the brightness tolerance value) of a second brightness value of the second pixel. In some embodiments, the brightness tolerance may be within a range having upper and lower values including 5% of the maximum brightness, 7%, 9%, 11%, 13%, 15%, 17%, 19%, 20%, or any value therebetween. For example, the brightness tolerance value may be between 5% and 20%. In another example, the brightness tolerance value may be between 7% and 15%. In yet another example, the brightness tolerance value may be about 10%.

All of the pixels in the first diffraction pattern image may be compared to the pixels in the second diffraction pattern image and a percentage of the pixels may be determined to be substantially the same. The first diffraction pattern may be substantially the same as a second diffraction pattern when a percentage of the pixels of the first diffraction pattern are substantially the same as the pixels of the second diffraction image. In some embodiments, the first diffraction pattern may be substantially the same as the second diffraction pattern when at least 70% of the pixels of the first diffraction pattern are substantially the same as the pixels of the second diffraction image. In other embodiments, the first diffraction pattern may be substantially the same as the second diffraction pattern when at least 80% of the pixels of the first diffraction pattern are substantially the same as the pixels of the second diffraction image. In further embodiments, the first diffraction pattern may be substantially the same as the second diffraction pattern when at least 90% of the pixels of the first diffraction pattern are substantially the same as the pixels of the second diffraction image.

Figure 7:
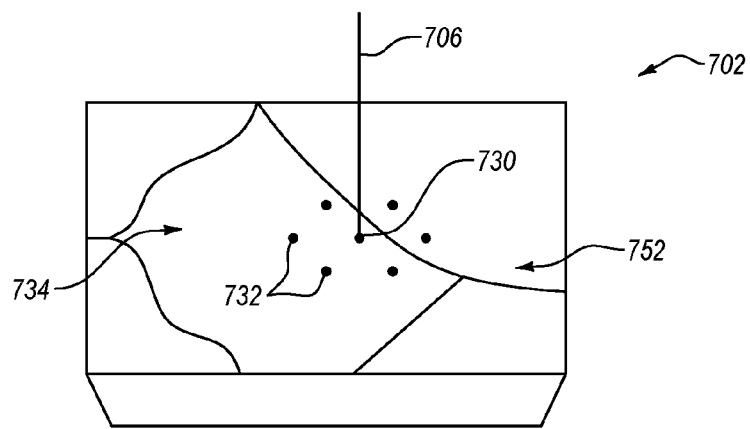
FIG. 7 depicts a plurality of sampling locations on a sample surface spanning a plurality of grains, according to at least one embodiment described herein.

FIG. 7 illustrates a schematic example of a plurality of sampling locations on a sample 702 that span a grain boundary from a first grain 734 to a second grain 752 and are distributed in a hexagonal grid. The first grain 734 may have a first crystallographic orientation and the second grain 752 may have a second crystallographic orientation. In some embodiments, the first crystallographic orientation may be different from the second crystallographic orientation. In other embodiments, the difference between the first crystallographic orientation and the second crystallographic orientation may be greater than a user-defined misorientation tolerance. A central sampling location 730 and/or adjacent sampling locations 732 may be sampled by the electron beam 706 to acquire a central diffraction pattern, as described in the present disclosure. The adjacent sampling locations 732 may be sampled relative to the central sampling location 730 during live acquisition or a full grid may be sampled to create a diffraction pattern image set, from which selected images may be acquired after live acquisition. As shown in the embodiment of FIG. 7, one or more of the adjacent sampling locations may be in a second grain 752.

Figure 8:
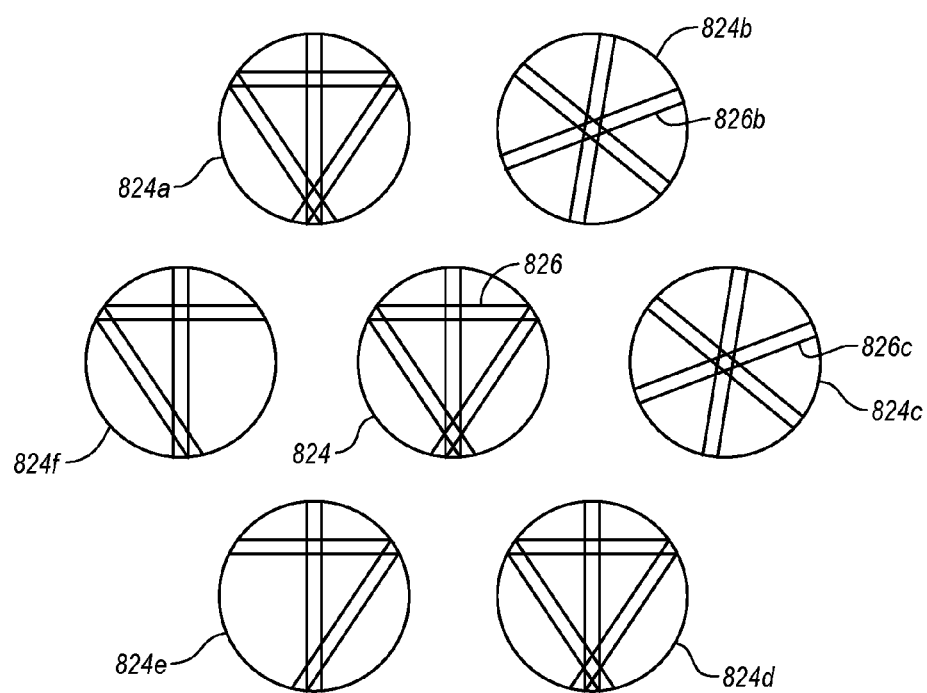
FIG. 8 is a schematic representation of an array of diffraction patterns having at least one uncorrelated diffraction pattern, according to at least one embodiment described herein.

FIG. 8 schematically depicts a central diffraction pattern 824 and a plurality of adjacent diffraction patterns 824a-f. In some embodiments, one or more of the adjacent diffraction patterns 824a-f may be acquired from a grain having a different crystal lattice than the central diffraction pattern 824. For example, the second adjacent diffraction pattern 824b and the third adjacent diffraction pattern 824c may exhibit a different calculated crystallographic orientation upon indexing of the diffraction pattern. The method 216 described in relation to FIG. 2 may average each of the depicted adjacent diffraction patterns weighted equally. The electron bands 826b of the second adjacent diffraction pattern 824b and the electron bands 826c third adjacent diffraction pattern 824c may be averaged with the electron bands 826 of the central diffraction pattern 824 and the first, fourth, fifth, and sixth adjacent diffraction patterns 824a, 824d, 824e, 824f. A resulting averaged diffraction pattern may reduce the brightness of the electron bands 826 of the central diffraction pattern 824 and may introduce the electron bands 826b, 826c of the second adjacent diffraction pattern 824b and the third adjacent diffraction pattern 824c. Indexing the resulting averaged diffraction pattern may result in a calculated crystallographic orientation that properly relates to the central diffraction pattern 824, but may introduce ambiguity and reduce a confidence index.

The method 616 described in relation to FIG. 6 may include indexing the central diffraction pattern 824 and index the second adjacent diffraction pattern 824b and the third adjacent diffraction pattern 824c. Comparing the calculated crystallographic orientation of the central diffraction pattern 824 against the calculated crystallographic orientation of the second adjacent diffraction pattern 824b and the third adjacent diffraction pattern 824c may allow for the second adjacent diffraction pattern 824b and the third adjacent diffraction pattern 824c to be excluded from the averaging of the central diffraction pattern 824 and the remaining adjacent diffraction patterns (i.e., the first, fourth, fifth, and sixth adjacent diffraction patterns 824a, 824d, 824e, 824f). As described herein, comparing the central diffraction pattern 824 to one or more adjacent diffraction patterns 824a-f may include comparing a brightness value of the pixels of the central diffraction pattern 824 against the pixels of the one or more adjacent diffraction patterns 824a-f. Comparing the brightness value of the pixels of the central diffraction pattern 824 against the pixels of the one or more adjacent diffraction patterns 824a-f may allow for the second adjacent diffraction pattern 824b and the third adjacent diffraction pattern 824c to be excluded from the averaging of the central diffraction pattern 824 and the remaining adjacent diffraction patterns (i.e., the first, fourth, fifth, and sixth adjacent diffraction patterns 824a, 824d, 824e, 824f).

Figure 9:
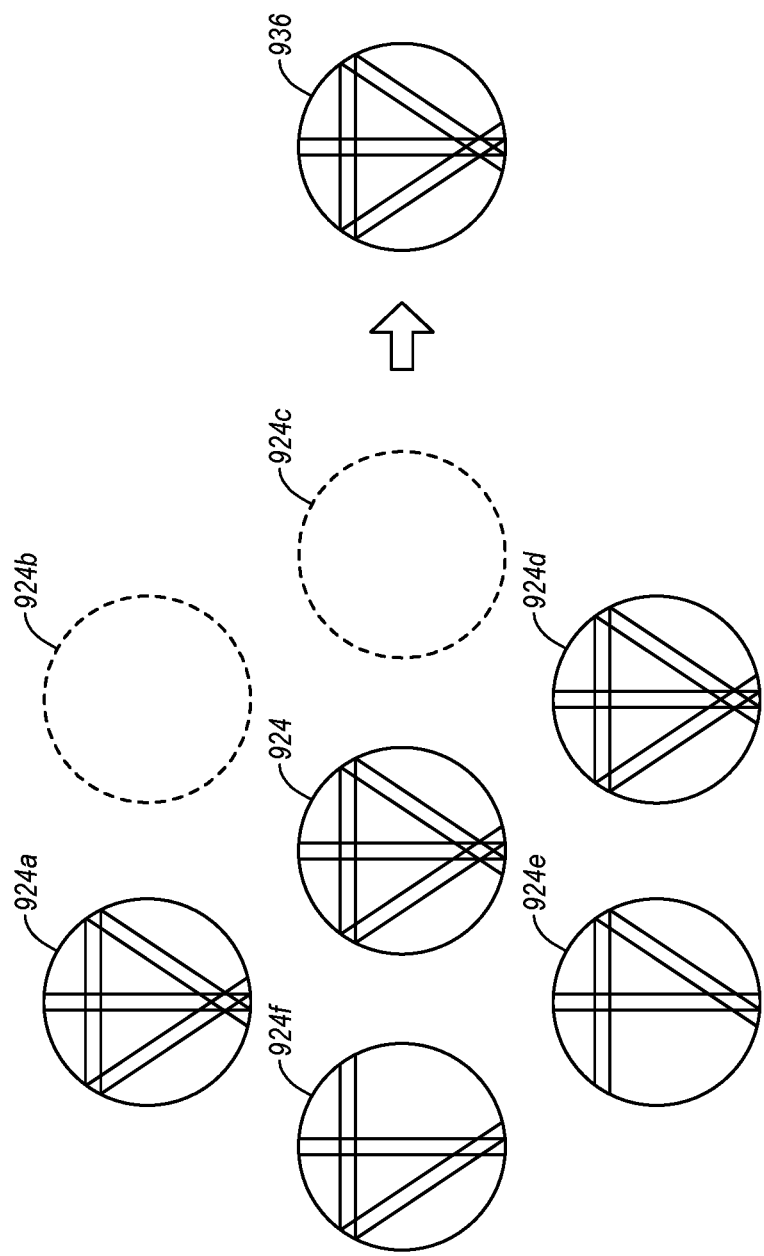
FIG. 9 is a schematic representation of spatially averaging correlated diffraction patterns, according to at least one embodiment described herein.

FIG. 9 schematically shows the averaging of a central diffraction pattern 924 with a first, fourth, fifth, and sixth adjacent diffraction patterns 924a, 924d, 924e, 924f while excluding a second adjacent diffraction pattern 924b and a third adjacent diffraction pattern 924c from the averaging process. The resulting averaged diffraction pattern 936 may incorporate one or more features of the central diffraction pattern 924 and the first, fourth, fifth, and sixth adjacent diffraction patterns 924a, 924d, 924e, 924f. The resulting averaged diffraction pattern 936 may have an increased signal to noise ratio relative to the central diffraction pattern 924 without introducing one or more artifacts of electron bands and/or diffraction patterns acquired from different crystal lattices or grains of a sample.

Figure 10:
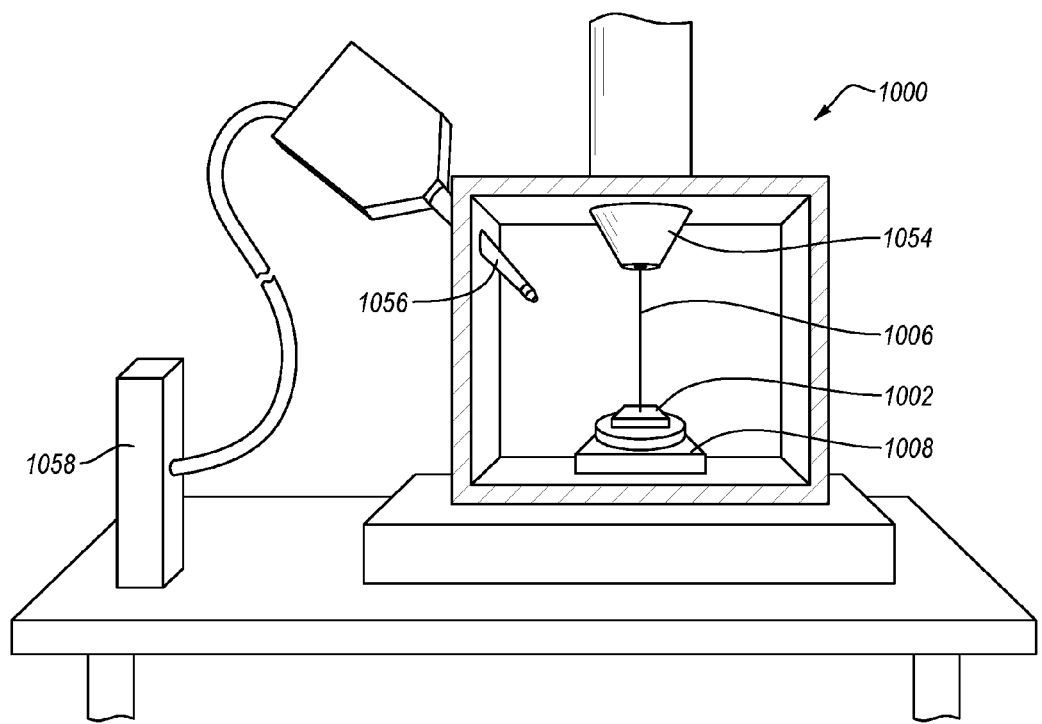
FIG. 10 is a side partial cutaway of an embodiment of an energy dispersive spectrometry ("EDS") detector in an SEM, according to at least one embodiment described herein.

As shown in FIG. 10, conventional EDS may be conducted in an SEM 1000 by presenting a sample 1002 in line with an electron beam 1006 and below the column 1054. While the present disclosure may describe one or more embodiments in relation to an SEM, it should be understood that at least some of the systems and methods presented herein are equally applicable to a TEM. The surface of the sample 1002 may be oriented perpendicularly to the electron beam 1006 or may be oriented at an angle not perpendicular to the electron beam 1006. For a sample 1002 with an uneven surface, tilting of the sample provides line-of-sight to features that are otherwise inaccessible by the electron beam 1006. The position of the sample 1002 relative to the electron beam 1006 may be achieved by tilted a sample stage 1008 or by providing a sample holder (not shown) having non-parallel surfaces mounted to the sample stage 1008 or a combination of the two.

The interaction of the electron beam 1006 and the sample 1002 causes the atoms of the sample 1002 to become excited. When an electron or electrons of an atom relaxes to a lower-energy ground state, the atom will emit energy in the form of an x-ray. The x-ray will have a particular energy that correlates to the state of the electron that emitted the x-ray. For example, electrons in the K energy level of the atom will emit an x-ray with a different energy than electrons in the L energy level. The x-rays will also vary in energy depending on the element emitting the x-ray. For example, electrons of the K energy level in aluminum will emit x-rays of different energy than the electrons of the K energy level in iron. Measurement of the x-ray energy allows for differentiation of elements excited by the electron beam 1006. The relative quantity of x-ray counts in a given period of time indicates relative concentration of those elements in the sample 1002 excited by the electron beam 1006.

The EDS detector 1056 includes a detection surface that converts x-rays into a voltage signal. The voltage signal is the provided to a pulse processor that measures the signal and passes them to an analyzer 1058, which may then display the data and allow further analysis by a user. The detection surface can be a semiconductor that is cooled to low temperatures, for example, by liquid nitrogen, Peltier cooling, other cooling methods, or combinations thereof. In some embodiments, the EDS detector 1056 may include a silicon-lithium ("Si(Li)") detector, a silicon drift detector ("SDDs"), or other x-ray sensitive detectors.

Rastering the electron beam 1006 across the surface of a sample 1002 allows for the collection of x-ray count maps of the surface. The x-ray maps can include individually selected energy channels or each data point within the map can include a full spectrum for the point. Calculating the relative concentrations of various elements in the sample 1002 is performed by comparing the relative intensities of energy channels having local maximum in the x-ray spectrum of each point.

During x-ray mapping of a sample 1002, the individual sampling locations of the surface have relatively low quantities of x-ray counts detected by the EDS detector 1056. The relatively low x-ray counts result in low-resolution spectra and/or poor statistical quality of the elemental identification. Recent advancements in EDS detectors 1056 have allowed increased collection rates of x-ray counts and SEM 1000 improvements have allowed for greater current to be applied to the sample 1002 by the electron beam 1006. The spectral information collected by the EDS detector 1056 may be at least partially limited by the physical collection area of the detection surface in the EDS detector 1056 and by the energy resolution that the EDS detector 1056 can maintain as throughput increases. The typical x-ray count rates of a SDD are about 10,000 to in excess of 1,000,000 counts per second. While collection rates have increased in recent years, improvements to statistics, particularly early in the scan of a sample 1002, are desirable.

Figure 11:
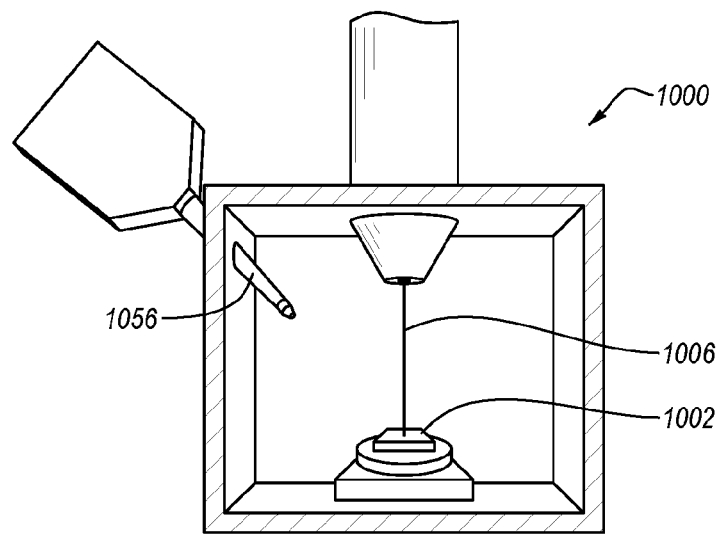
FIG. 11 depicts an application of an electron beam to sample in the SEM of FIG. 1, according to at least one embodiment described herein.

The spectrum of x-ray energies may represent at least some of the elements present in a sample. The spectrum may include a plurality of energy channels that each contain a number of x-ray counts corresponding to the quantity of x-rays detected by the EDS detector within the energy channel. The EDS detector and sample may be connected to a scanning electron microscope ("SEM") during operation. The x-rays detected by the EDS detector may be at least partially dependent upon the conditions of the SEM during collection of x-rays. For example, FIG. 11 depicts the SEM 1000 containing the sample 1002 held in a low pressure and/or near vacuum environment and the EDS detector 1056 mounted to the SEM 1000 in the direction of the sample 1002. The SEM 1000 may provide an electron beam 1006 that is accelerated towards and focused at the sample 1002. The electron beam may have a variety of accelerating voltages and a variety of beam currents. The accelerating voltage may affect the energy of the x-rays generated during interaction of the electron beam 1006 with the sample 1002. The beam current may affect the quantity of x-rays generated during interaction of the electron beam with the sample 1002.

Figure 12:
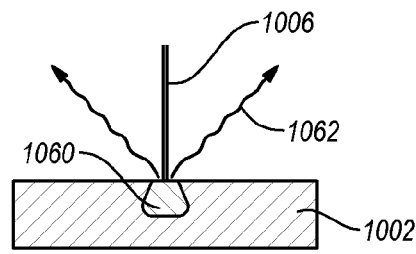
FIG. 12 depicts an interaction volume within the sample and x-rays generated therein, according to at least one embodiment described herein.

FIG. 12 depicts the interaction of the electron beam 1006 with the sample 1002. The electron beam 1006 consists of the electrons from an electron source accelerated toward the sample. As used herein "electron source" should be understood to refer to any emitting source of electrons, such as a thermal field emission gun ("FEG") source, a cold FEG source, a tungsten filament source, a $LaB_6$ source, or other electron emission sources. The electrons emitted by the electron source may be accelerated through a magnetic field to an energy in a range having upper and lower values including any of 0.5 kilovolts ("kV"), 1 kV, 5 kV, 10 kV, 15 kV, 20 kV, 25 kV, 30 kV, 50 kV, 1000 kV, 1100 kV, 300 kV, or any value therebetween. For example, the incident electrons may have an incident energy between 0.5 kV and 300 kV. In another example, the incident electrons may have an incident energy between 1 kV and 30 kV.

The electron beam 1006 may contact the sample 1002 as an approximate point source, but interact with the sample 1002 in an interaction volume 1060. As used herein, "point source" should be understood to refer to an approximation of a singular origin point for the energy. While the electron beam may be practically limited to have an incident diameter greater than about 3 nanometers ("nm"), the electrons of the electron beam 1006 will scatter upon contact with the sample 1002, producing a larger interaction volume 1060. The interaction volume 1060 is the volume in which the electrons of the electron beam 1006 will interact with the sample and impart energy to the atoms of the sample 1002.

In other embodiments, the sample may be a thin-section, such as that used in conventional TEM imaging. A thin-section sample may be less than 100 nm thick (i.e., in the direction substantially perpendicular to the surface to be imaged. A thin-section may, therefore, limit the expansion of the interaction volume. For example, as the electron beam 1006 contacts the thin-section, electrons of the electron beam 1006 may begin to scatter and interact with atoms of the thin-section in a broader area and larger volume than the diameter of the electron beam 1006. In contrast, a bulk sample ("bulk sample," in this case, referring to a sample thick enough to prevent penetration by the electron beam and/or the interaction volume 1060), the thin-section sample may allow electrons to penetrate through the sample, limiting or preventing further lateral expansion of the interaction volume. The use of thin-section samples may allow greater spatial resolution of the spectrometry in combination with an associated reduction in x-ray generation.

The electron beam 1006 may transfer energy to the sample 1002 by exciting the atoms of the sample 1002. The incident electrons of the electron beam 1006 may transfer energy to and/or displace electrons from the atoms of the sample 1002 causing at least some of the atoms of the sample 1002 to be in an unstable or excited state. When the electrons of the excited atoms return to a lower-energy ground state, the excess energy is released as an x-ray 1062 that is emitted from the sample 1002. The energy of the x-ray 1062 is correlated to the atomic composition of the excited atom. For example, the energy of the x-ray emitted is affected by the electron orbitals of the atom and the nuclear composition (i.e., element). The energy of an x-ray emitted by the K-energy level of an aluminum atom will be different than the energy of an x-ray emitted by the K-energy level of a titanium atom. Further, the energy of an x-ray emitted by the K-energy level of an aluminum atom will be substantially constant.

Figure 13:
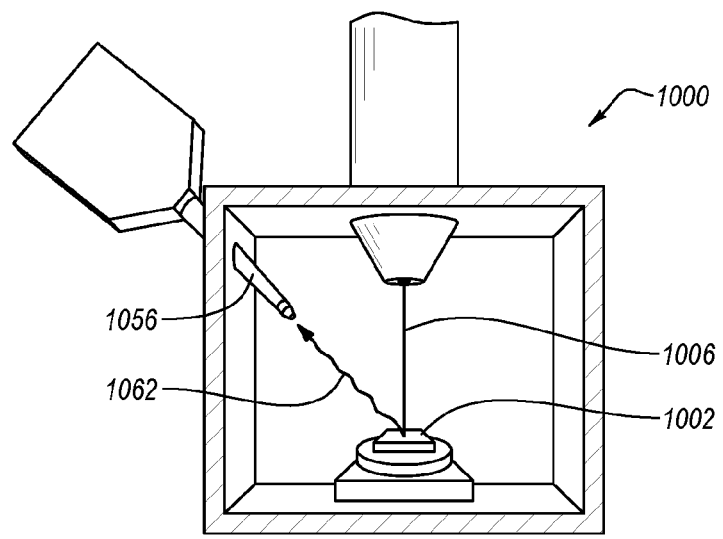
FIG. 13 depicts an x-ray being emitted from the sample toward the EDS detector, according to at least one embodiment described herein.

FIG. 13 depicts the detection of an x-ray 1062 by the EDS detector 1056. The EDS detector 1056 may detect ambient x-rays from the environment during operation that constitute a background noise in the system, while the x-rays 1062 emitted by the sample 1002 due to interaction with the electron beam 1006 and detected by the EDS detector 1056 constitute the signal in the EDS detector 1056. The larger size of the interaction volume 1060 shown in FIG. 12 may also introduce an interfering signal to the spectrum. For example, the electron beam 1006 may be focused on a particular sampling location on a surface of the sample; while the interaction volume 1060 may be larger than the area of interest and may result in x-rays 1062 generated from areas not intended to be excited by the electron beam 1006.

Figure 14:
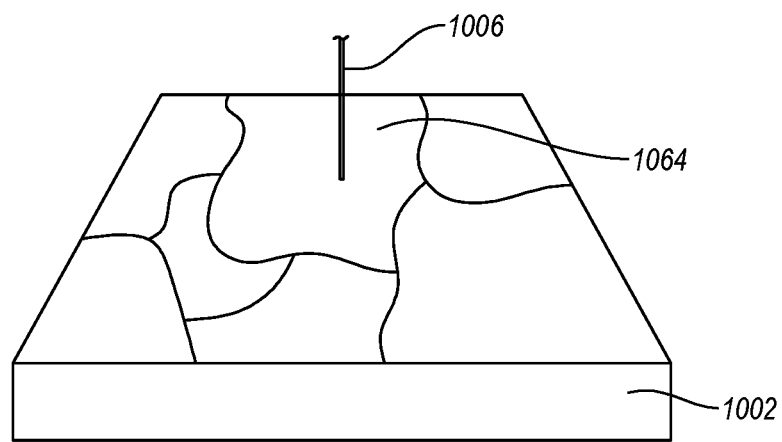
FIG. 14 is a schematic representation of an electron beam exciting a specific sampling location on a sample, according to at least one embodiment described herein.
Figure 15:
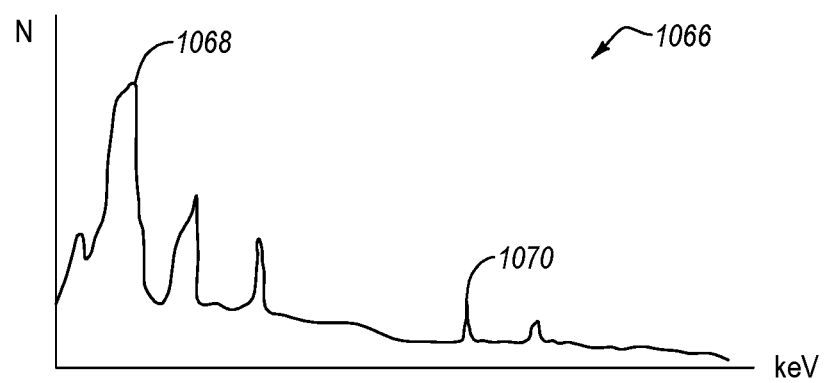
FIG. 15 is a schematic representation of an x-ray spectrum collected from the sampling point of FIG. 14, according to at least one embodiment described herein.

FIG. 14 is a schematic representation of the surface of the sample 1002 contacted by the electron beam 1006. The electron beam 1006 may be focused on a first phase 1064 of the sample 1002. The sample 1002 may be a multi-phase sample with a plurality of chemically-distinct phases therein. In the depicted example, the individual phases are larger than the interaction volume of the electron beam 1006. The first phase 1064 may emit x-rays that correspond to the elemental composition of the first phase 1064 and the EDS detector 1056 may detect the x-rays to produce a first spectrum 1066, such as shown in FIG. 15.

The first spectrum 1066 may depict the quantity of detected x-rays (N) as a function of the energy (keV) of the detected x-rays. A local maximum of the spectrum may be an energy peak that corresponds to an emission energy of an element present in the first phase 1064. For example, the first energy peak 1068 of the first spectrum 1066 may correspond to a lighter element than the second energy peak 1070. In another example, the second energy peak 1070 may correspond to a different electron energy-level of the same element as the first energy peak 1068.

In some embodiments, the elemental energy peaks may not be local maxima, such as the "shoulder" on the lower energy side (i.e., left side) of the first energy peak 1068. The shoulder may be due to another element with a lower x-ray energy in a lower concentration than the element responsible for the dominant first energy peak 1068. The identified energy peaks may provide a measured element list that lists and presents the elements in the sample 1002 that emitted x-rays 1062 detected by the EDS detector 1056. In yet other embodiments, a region of interest ("ROI") may be selected by defining a lower and upper energy limit and all x-ray counts that fall within the ROI may be considered to be affiliated with a particular emission source, such a particular element. As used herein, references to "comparing" or "comparisons" between spectra should be understood to include comparing or comparisons between any of energy peaks, peak identifications, element lists, ROI counts, other statistics of the spectra, or combinations thereof.

Figure 16:
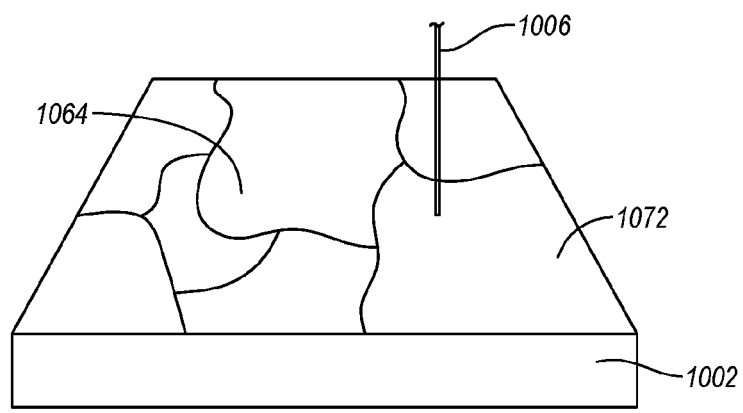
FIG. 16 depicts another sampling location on the sample surface of FIG. 14 in a different grain, according to at least one embodiment described herein.
Figure 17:
FIG. 17 is a schematic representation of an x-ray spectrum collected from the sampling point of FIG. 16, according to at least one embodiment described herein.

FIG. 16 depicts the electron beam 1006 focused on another location on the surface of the sample 1002. The electron beam 1006 may be focused on a second phase 1072 of the sample 1002. In the depicted embodiment, the second phase 1072 is adjacent to the first phase 1064. The second phase 1072 may include some of the same elements as the first phase 1064 or different elements. The electron beam 1006 may impart energy to the second phase 1072 and the EDS detector 1056 may receive emitted x-rays 1062 may produce the second spectrum 1074 depicted in FIG. 17.

Figure 18:
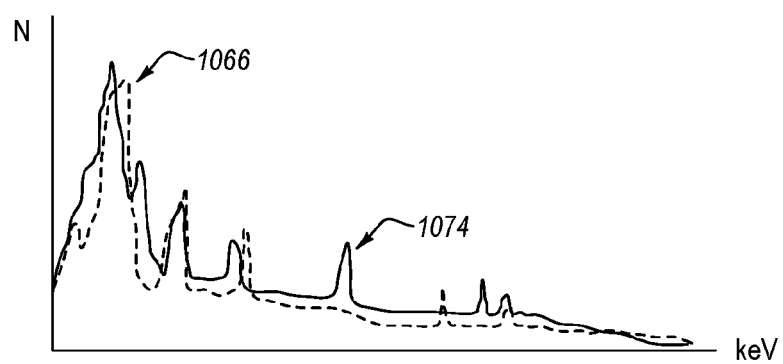
FIG. 18 is an overlay of the x-ray spectra of FIG. 15 and FIG. 17, according to at least one embodiment described herein.

FIG. 18 shows a comparison of the first spectrum 1066 and the second spectrum 1074. The x-ray counts "under" the energy peaks indicate a similar background noise between the first spectrum 1066 and second spectrum 1074. The first spectrum 1066 and the second spectrum 1074 may share one or more energy peaks, as well, indicating shared elements between the elemental compositions of the first phase 1064 and second phase 1072. For example, the shoulder of the first spectrum 1066 appears to be a discrete energy peak of the second spectrum 1074.

During mapping of a surface of the sample 1002, the electron beam 1006 may be moved relatively rapidly over the surface of the sample 1002. In such instances, the duration of time that the sample 1002 may emit x-rays 1062 from each sampling location may be limited and the overall quantity of x-rays 1062 detected by the EDS detector 1056 may be relatively low versus the background noise. With relatively low x-ray counts in the EDS detector 1056, a first spectrum 1066 such as that in FIG. 15 may yield unclear peak identifications and, therefore, uncertain elemental analysis and/or element lists.

The ability to aggregate spectral information between sampling locations may provide more accurate data more rapidly and earlier in the process of mapping a region of a sample 1002 with an EDS detector 1056. As used herein, "spectral information" should be understood to refer to any data associated with the collection and/or detection of x-rays 1062 emitted by the sample 1002 during interaction with an electron beam 1006 or other electron source. In some embodiments, the spectral information may include x-ray counts per energy channel, total x-ray counts, x-ray energy, identified energy peaks, background noise, counts-per-second information, other information regarding the collected spectrum, or combinations thereof. The aggregation of the spectral information may include a variety of statistical combinations of the spectral information.

In some embodiments, aggregating the spectral information may include averaging the spectral information of a plurality of spectra. In other embodiments, aggregating the spectral information may include summing together the spectral information of a plurality of spectra. In yet other embodiments, aggregating the spectral information may include averaging the spectral information based on a weighted average of a plurality of spectra.

Figure 19:
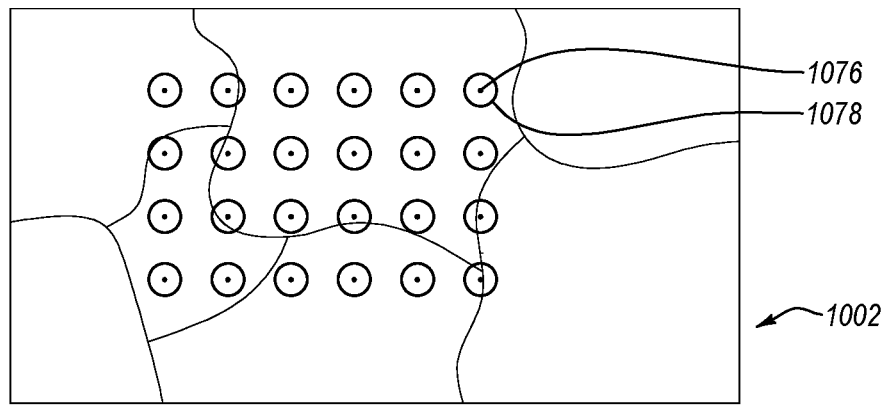
FIG. 19 is a schematic representation of an array of sampling locations and associated interaction volumes, according to at least one embodiment described herein.

As shown in FIG. 19, in some embodiments, the electron beam 1006 may be moved relative to the surface of the sample 1002 in a grid-like pattern to place the electron beam at a plurality of sampling locations 1076 on the sample 1002. Each sampling location 1076 has an associated interaction diameter 1078 (due to the subsurface interaction volume 1060 described in relation to FIG. 12). In some embodiments, the sampling locations 1076 may be located on a square grid on the surface of the sample 1002. In other embodiments, the sampling locations 1076 may be located on a hexagonal grid on the surface of the sample 1002. In yet other embodiments, the sampling locations 1076 may be located on a circular or spiral grid on the surface of the sample 1002. In still other embodiments, the sampling locations 1076 may be located in an irregular pattern or set of locations on the surface of the sample 1002. The sampling locations 1076 may each have spectral information associated with the sampling location 1076 collected during sampling.

Figure 20:
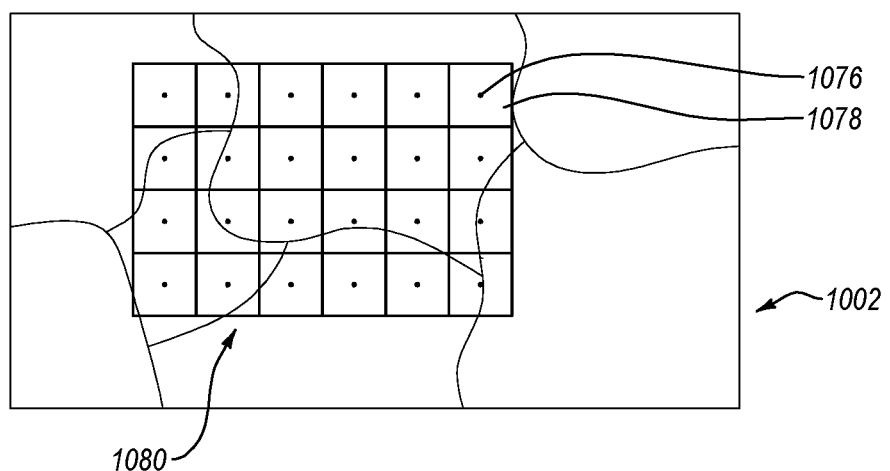
FIG. 20 depicts a map constructed of the sampling locations of FIG. 19; according to at least one embodiment described herein.

As shown in FIG. 20, the sampling locations 1076 may be compiled in a map 1080 that approximates the surface of the sample 1002. A map 1080 with a greater number of sampling locations 1076 may provide greater spatial resolution to better approximate the surface of the sample 1002 and borders between phases. For example, the depicted map 1080 has a plurality of sampling locations that, while containing information from only one phase, may spatially overlap another phase. In other places, the sampling locations 1076 may sample from multiple phases simultaneously, resulting in spectral information that may be misleading. However, increasing the number of sampling locations 1076 in a map 1080 may cause the dwell time at each sampling location to be reduced and, hence, may reduce the total spectral information and the quality of the spectral information statistics at each sampling location 1076.

Figure 21:
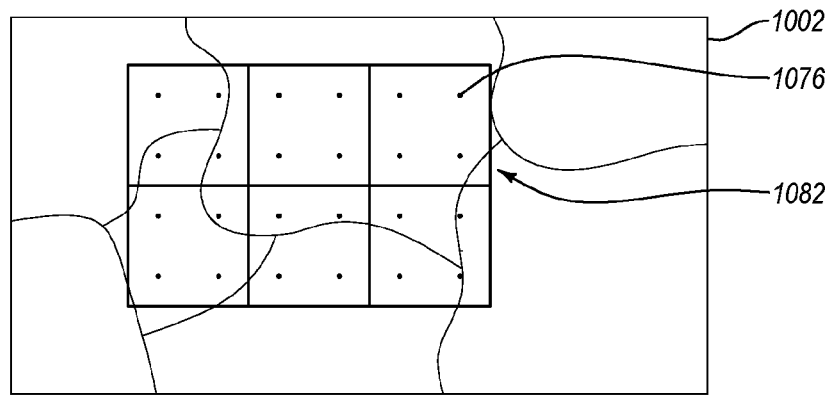
FIG. 21 depicts statistical binning of the sampling locations of FIG. 19; according to at least one embodiment described herein.

The spectral information at each sampling location 1076 may be aggregated with spectral information from adjacent sampling locations 1076 to provide a greater sampling size of the sample 1002 during the creation of a map 1080. For example, a binned map 1082, such as depicted in FIG. 21, may be created by aggregating the spectral information of sampling locations 1076. For example, the binned map 1082 may include sampling locations 1076 binned into 2×2 areas (measured by the number of sampling locations included in each dimension of the area). The binned map 1082, in other embodiments, may include binned regions of 3×3, 4×4, 5×5, or other size binned areas. In yet other embodiments, the binned regions may have unequal dimensions, such as 2×3, 4×2, 3×5, or other combinations. The binning may provide increased spectral information for the binned regions in the binned map 1082 compared to the individual sampling locations 1076.

Figure 22:
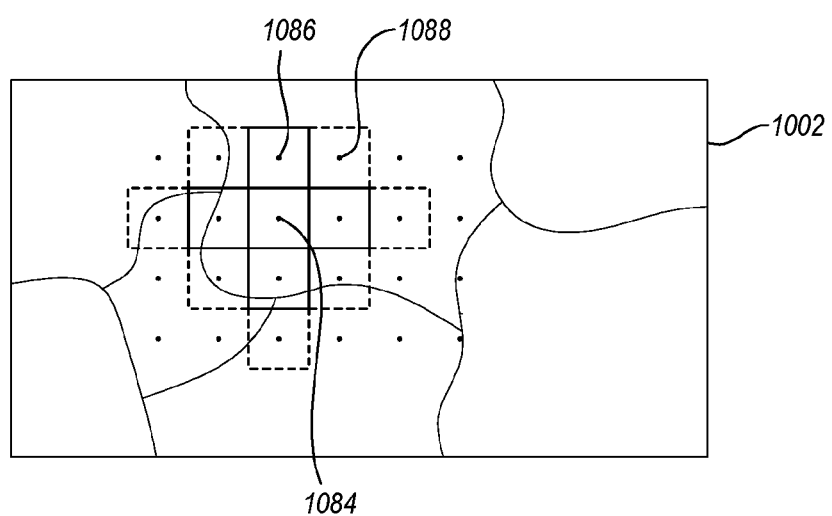
FIG. 22 depicts first-order spatial aggregation of the sampling locations of FIG. 19; according to at least one embodiment described herein.

The binned map 1082 may aggregate spectral information from sampling locations 1076 in disparate phases or surfaces. The spectral information of the sampling locations 1076 may be aggregated by spatial relationship to a central sampling location. Referring now to FIG. 22, a central sampling location 1084 may be a center of a kernel of sampling locations. For example, the central sampling location 1084 may have a plurality of first order adjacent sampling locations 1086. The first order adjacent sampling locations 1086 may be immediately adjacent the central sampling location 1084, such that the first order adjacent sampling locations 1086 are immediately adjacent in the x-direction and y-direction. The central sampling location 1084 may have second order adjacent sampling locations 1088 (shown in dashed lines) diagonally from the central sampling location 1084 and/or adjacent to a distal side of the first order adjacent sampling locations 1086.

The spatially aggregated spectra may be weighted in relation to the sampling position's location relative to the central sampling location 1084. In some embodiments, the central sampling location 1084 may be associated with a central spectrum, such as the first spectrum 1066 described in relation to FIG. 15. The adjacent sampling locations, including the first order adjacent sampling locations 1086 and second order adjacent sampling locations 1088, may each have an adjacent spectrum associated therewith.

The central spectrum may be aggregated with one or more of the adjacent spectra to create an aggregated spectrum. In some embodiments, the aggregated spectrum may have increased and/or improved statistics compared to the central spectrum. In other embodiments, the aggregated spectrum may have increased and/or improved signal-to-noise ratio of the central spectrum. For example, aggregating the central spectrum with one or more adjacent spectra by summing the x-ray counts in individual energy channels of the central spectrum and the adjacent spectra may increase the overall number of counts in the spectrum. In another example, aggregating the central spectrum with one or more adjacent spectra by averaging the x-ray counts in individual energy channels of the central spectrum and the adjacent spectra may increase the signal-to-noise ratio in the spectrum. The energy peaks of the aggregated spectrum may be identified to provide an aggregated element list. The aggregated element list may be compared to the measured element list to verify that the elements present in the original central spectrum are not significantly altered by the aggregation of the spectral information.

In some embodiments, the central spectrum may be aggregated with one or more adjacent spectra by a weighted aggregation. The weight aggregation may include summing the central spectrum with a fraction of the amplitude of the adjacent spectra determined by a weighting factor. For example, the quantity of x-ray counts of an energy channel of the central spectrum may be summed together with a fraction of the x-ray counts of the corresponding energy channel of the adjacent spectrum. The central spectrum may, therefore contribute more to the aggregated spectrum than the adjacent spectrum, but the adjacent spectrum may still influence the statistics. This may be beneficial in samples that exhibit zoning or elemental migration effects. In some embodiments, the weighting factor may be in a range having upper and lower values including any of 0.5, 0.55, 0.6, 0.65, 0.7, 0.75, 0.8, 0.85, 0.9, 0.95, 1.0, or any value therebetween. For example, the weighting factor may be in a range of 0.5 to 1.0. In another example, the weighting factor may be in a range of 0.6 to 0.9. In yet another example, the weighting factor may be in a range of 0.7 to 0.85. In a further example, the weighting factor may be 0.8.

In embodiments having a plurality of orders of adjacent sampling locations (e.g., first order adjacent sampling location 1086, second order adjacent sampling location 1088, etc.), the first order adjacent sampling location 1086 may have a first weighting factor and the second order adjacent sampling location 1088 may have a second weighting factor. The first weighting factor may be equal to or greater than the second weighting factor. In the depicted example, the first and second weighting factors may reduce the effect on a central spectrum of an adjacent spectrum reflecting a different phase than the central spectrum.

In other embodiments, spectra from non-adjacent sampling locations may be aggregated based on similar spectral information. Spectral information may be collected from sampling locations on a sample consisting of a plurality of particles deposited on a substrate. A forensic analysis of residue, for example, may include depositing tens, hundreds, or thousands of particles on a substrate for analysis. Each particle may be analyzed a plurality of sampling locations using a system or method described herein to aggregate a representative aggregated spectrum from adjacent sampling locations on each particle. Aggregating multiple spectra from a single particle may help compensate for x-ray emission and/or detection due to surface variations. The spectra from different particles may be aggregated together into a representative aggregated phase spectrum to provide increased overall x-ray counts and statistics for each phase of particles and/or to assist with subsequent phase matching for particle analysis.

In another embodiment, the central spectrum may be compared against each of the one or more adjacent spectra prior to aggregation of the central spectrum and the one or more adjacent spectra to create an aggregated spectrum. Similarly to the comparison shown in FIG. 18, a central spectrum may be compared to each of the one or more adjacent spectra and attempt to match the position and/or intensity of energy peaks identified in each of the central spectrum and the adjacent spectrum. The intensity of each energy channel of the spectra may be compared to one another.

In some embodiments, the intensity of each channel may be compared to one another and a percentage deviation within the energy channel (the difference may be calculated as a percentage difference from the central spectrum energy channel intensity) may be calculated. In another embodiment, the difference in an energy channel from the central spectrum to the adjacent spectrum may be calculated as a nominal value (a quantity of x-ray counts difference between the central spectrum energy channel intensity and the corresponding adjacent spectrum energy channel intensity) that then compared to the overall counts of the central spectrum to calculate the percentage deviation of the energy channel counts from the total counts. For example, an energy channel with 1000 counts in the central spectrum and 50 counts in the adjacent spectrum may be a 50% deviation in the first embodiment, but may be only a 0.5% deviation when the central spectrum has 10,000 counts total.

In embodiments including a comparison of the central spectrum to the adjacent spectrum, the percentage deviation may be compared to a threshold value prior to aggregation of the central spectrum and the adjacent spectrum. If the percentage deviation is less than the threshold value, the central spectrum and adjacent spectrum may be aggregated. If the percentage deviation is greater than the threshold value, the adjacent spectrum may be ignored during the aggregation of the central spectrum and one or more other adjacent spectra. Ignoring an adjacent spectrum that does not match the central spectrum to within a threshold value may limit or prevent the aggregation of spectra from dissimilar phases in the sample. In yet other embodiments, binning may be combined with spectral comparison to allow selective spatial aggregation of binned spectra.

The energy peaks of the spectrum of each sampling location 1076 may also be identified to produce an element list for each sampling location 1076. The element lists of each sampling location 1076 may be compared against one another to identify potential phases in the sample 1002. The coarse identification of phases based on the element lists of each sampling location 1076 may be used to limit the aggregation of spectra to those within the same phase.

Figure 23:
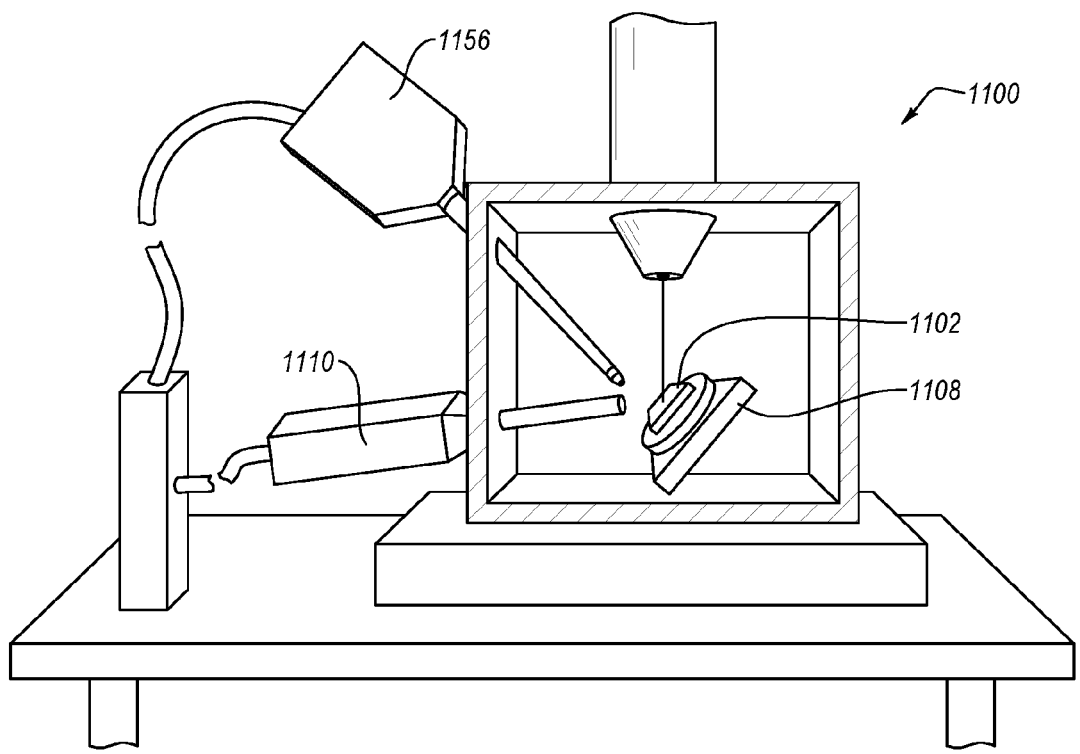
FIG. 23 depicts an embodiment of an EDS detector and an electron backscatter diffraction ("EBSD") detector in an SEM, according to at least one embodiment described herein.

In yet other embodiments, the collection of spatial aggregation of spectral information may be combined with simultaneous spatial aggregation of electron backscatter diffraction information. As shown in FIG. 23, an SEM 1100 may include an EDS detector 1156 and an EBSD detector 1110. The sample 1102 may be mounted on a tiltable sample stage 1108.

Figure 24:
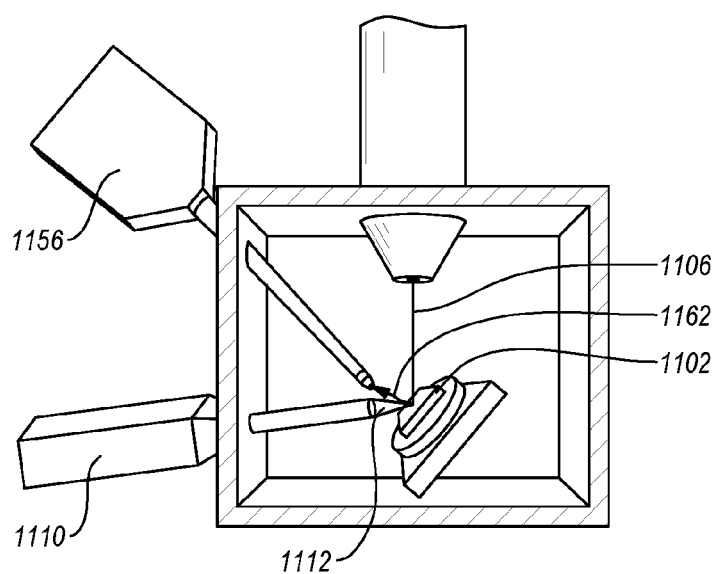
FIG. 24 depicts simultaneous collection of x-ray counts and diffraction patterns, according to at least one embodiment described herein.

An SEM 1100 having both an EDS detector 1156 and an EBSD detector 1110 may allow for simultaneous collection of an EDS spectrum and diffraction pattern at each sampling location. The simultaneous collection may allow for additional information regarding phases to be collected. As shown in FIG. 15, conventional EBSD may be conducted in the SEM 1100 by presenting the surface of the sample 1102 at an angle to an electron beam 1106. The angle may be any angle within a range of values from 5° to 50° degrees and, most commonly, 20° to the electron beam 1106. As shown in FIG. 24, the position of the sample 1102 relative to the electron beam 1106 may be achieved by tilted a sample stage 1108 approximately 70° from level or by providing a sample holder (not shown) having non-parallel surfaces mounted to the sample stage 1108 or a combination of the two. The angle of the surface of the sample 1102 relative to the electron beam 1106 allows electrons from the electron beam 1106 to enter a portion of the sample 1102. In the sample 1102, electrons of the electron beam 1106 diffract from crystal planes. The diffracted electrons 1112 travel from the diffraction volume toward the EBSD detector 1110 in a geometric pattern of relative intensities of the diffracted electrons 1112. The diffracted electrons 1112 may be measured to calculate the relationship of crystal planes within the interaction volume and, therefore, an orientation of the crystal planes in space relative to the sample surface or other known orientation. The electrons of the electron beam 1106 may also excite the sample 1102 and the sample 1102 may emit x-rays 1162 that may be detected by the EDS detector 1156.

In some embodiments, the spectral information collected by the EDS detector 1156 simultaneously with the diffraction patterns collected by the EBSD detector 1110 at each sampling location may be used to spatially average and/or aggregate the diffraction patterns collected by the EBSD detector 1110. In other embodiments, the diffraction patterns collected by the EBSD detector 1110 simultaneously with the spectral information collected by the EDS detector 1156 at each sampling location may be compared against one another and may be used to spatially average and/or aggregate the spectra collected by the EDS detector 1156.

Embodiments described herein may be implemented on various types of computing systems. These computing systems are now increasingly taking a wide variety of forms. Computing systems may, for example, be handheld devices, appliances, laptop computers, desktop computers, mainframes, distributed computing systems, or even devices that have not conventionally been considered a computing system. In this description and in the claims, the term "computing system" is defined broadly as including any device or system (or combination thereof) that includes at least one physical and tangible processor, and a physical and tangible memory capable of having thereon computer-executable instructions that may be executed by the processor. A computing system may be distributed over a network environment and may include multiple constituent computing systems.

As used herein, the term "executable instructions" or "executable component" can refer to software objects, routings, or methods that may be executed on the computing system. The different components, modules, engines, and services described herein may be implemented as objects or processes that execute on the computing system (e.g., as separate threads).

Figure 25:
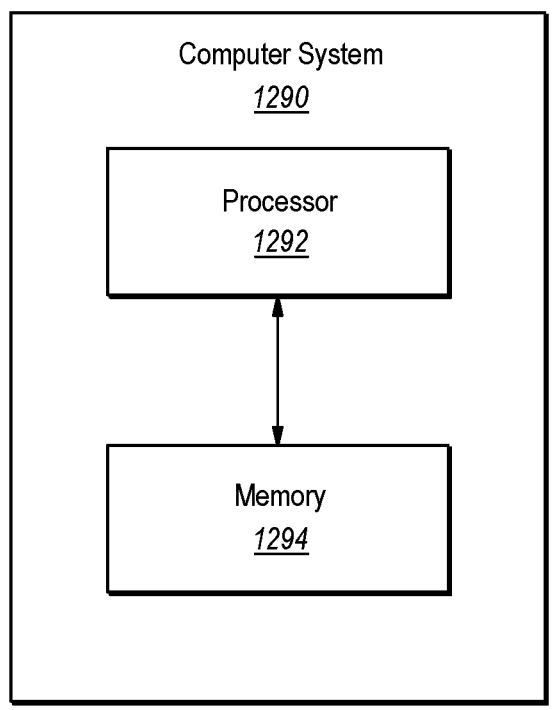
FIG. 25 is a schematic representation of a computing device having a processor and memory.

As illustrated in FIG. 25, a computing system 1290 typically includes at least one processor 1292 and memory 1294. The memory 1294 may be physical system memory, which may be volatile, non-volatile, or some combination of the two. The term "memory" may also be used herein to refer to non-volatile mass storage such as physical storage media or other data storage devices. If the computing system is distributed, the processing, memory, and/or storage capability may be distributed as well.

Embodiments of the methods described herein may be described with reference to acts that may be performed by one or more computing systems. If such acts are implemented in software, one or more processors of the associated computing system that performs the act direct the operation of the computing system in response to having executed computer-executable instructions. For example, such computer-executable instructions may be embodied on one or more computer-readable media that form a computer program product. An example of such an operation involves the manipulation of data. The computer-executable instructions (and the manipulated data) may be stored in the memory 1294 of the computing system 1290. Computing system 1290 may also contain communication channels that allow the computing system 1290 to communicate with other message processors over a wired or wireless network.

Embodiments described herein also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, embodiments described herein can comprise at least two distinctly different kinds of computer-readable media: computer storage media and transmission media.

Computer storage media are physical hardware storage media that store computer-executable instructions and/or data structures. Physical hardware storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the functionality disclosed herein.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. Any element of an embodiment described herein may be combined with any element of any other embodiment described herein. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A method for spatially averaging diffraction patterns comprising:

acquiring a central diffraction pattern and a plurality of adjacent diffraction patterns from an electron backscatter diffraction detector;

averaging the central diffraction pattern with one or more of the plurality of adjacent diffraction patterns to produce an averaged diffraction pattern; and indexing the averaged diffraction pattern to produce an averaged crystal orientation.

2. The method of claim 1, acquiring a central diffraction pattern and a plurality of adjacent diffraction patterns further comprising saving the central diffraction pattern and the plurality of adjacent diffraction patterns to a data storage device.

3. The method of claim 1, averaging the central diffraction pattern with one or more of the plurality of adjacent diffraction patterns further comprising averaging a pixel intensity of the central diffraction pattern with a correlated pixel intensity of the at least one of the plurality of adjacent diffraction patterns.

4. The method of claim 1, averaging the central diffraction pattern with one or more of the plurality of adjacent diffraction patterns further comprising averaging an electron band position of the central diffraction pattern with a correlated electron band position of the at least one of the plurality of adjacent diffraction patterns.

5. The method of claim 1, the adjacent diffraction patterns being collected from sampling locations on a hexagonal grid.

6. The method of claim 1, indexing the averaged diffraction pattern further comprising calculating an averaged confidence index.

7. The method of claim 1, further comprising indexing the central diffraction pattern to produce a measured crystal orientation.

8. The method of claim 7, further comprising comparing the measured crystal orientation to the averaged crystal orientation.

9. A system for spatially averaging diffraction patterns comprising:
   an electron backscatter detector;
   one or more hardware processors in data communication with the electron backscatter detector; and
   one or more storage devices having stored computer-executable instructions which, when executed by the one or more hardware processors, are configured to cause the computing system to perform a method including:
      acquiring a central diffraction pattern;
      acquiring a plurality of adjacent diffraction patterns;
      comparing the central diffraction pattern to one or more of the plurality of adjacent diffraction patterns;
      averaging at the central diffraction pattern with one or more of the plurality of adjacent diffraction patterns to produce an averaged diffraction pattern; and
      indexing the averaged diffraction pattern to produce an averaged crystal orientation.

10. The system of claim 9, wherein the method further comprises:
    indexing the central diffraction pattern to produce a measured crystallographic orientation;
    indexing at least one of the plurality of the adjacent diffraction patterns to produce an adjacent crystallographic orientation; and
    wherein comparing the central diffraction pattern to one or more of the plurality of adjacent diffraction patterns comprises comparing the measured crystal orientation with the adjacent crystal orientation against a misorientation tolerance.

11. The system of claim 9, indexing the central diffraction pattern further comprising calculating a measured confidence index.

12. The system of claim 11, indexing the averaged diffraction pattern further comprising calculating an averaged confidence index, and further comprising comparing the averaged confidence index and the measured confidence index and determining a lower value of the averaged confidence index and the measured confidence index.

13. The system of claim 12, wherein the method further comprises discarding data associated with the lower value.

14. The system of claim 9, acquiring a central diffraction pattern further comprising collecting a diffraction pattern from a sample.

15. The system of claim 9, acquiring a plurality of adjacent diffraction patterns further comprising collecting a plurality of diffraction patterns from a sample.

16. A method for calculating crystallographic orientations comprising:
    acquiring a diffraction pattern set having a plurality of diffraction patterns therein;
    indexing a plurality of the diffraction patterns to calculate one or more misorientations;
    correlating a plurality of misorientations to identify one or more grains;
    averaging a central diffraction pattern with one or more adjacent diffraction patterns based upon the one or more grains to produce an averaged diffraction pattern; and
    indexing the averaged diffraction pattern to produce an averaged orientation.

17. The method of claim 16 further comprising calculating a confidence index for the averaged diffraction pattern.

18. The method of claim 17 further comprising indexing and calculating a confidence index for the central diffraction pattern, comparing the confidence index for the central diffraction pattern and the confidence index for the averaged diffraction pattern.

19. The method of claim 16, correlating a plurality of misorientations comprising identifying adjacent misorientations greater than 5°.

20. The method of claim 16, further comprising collecting a diffraction pattern set with an electron backscatter detector.

* * * * *